United States Patent
Feine

(12) 
(10) Patent No.: US 6,328,566 B1
(45) Date of Patent: Dec. 11, 2001

(54) ID SYSTEM FOR ULTRASONIC DENTAL INSERTS

(76) Inventor: James Feine, P.O. Box 2009, Bellaire, TX (US) 77402-2009

( * ) Notice: Subject to any disclaimer, the term of this patent is extended or adjusted under 35 U.S.C. 154(b) by 0 days.

(21) Appl. No.: 09/681,251

(22) Filed: Mar. 7, 2001

(51) Int. Cl.⁷ ........................................................ A61C 3/00
(52) U.S. Cl. .............................. 433/119; 310/26; 318/118
(58) Field of Search ........................ 433/119, 86; 310/26; 318/118

(56) References Cited

U.S. PATENT DOCUMENTS

| | | | |
|---|---|---|---|
| 3,526,036 | * 9/1970 | Goof ..................................... | 433/119 |
| 3,736,663 | * 6/1973 | White . | |
| 3,977,084 | * 8/1976 | Sloan . | |
| 4,253,830 | * 3/1981 | Kazen et al. ........................... | 433/77 |
| 4,310,310 | * 1/1982 | Bailey .................................... | 433/126 |
| 4,355,976 | * 10/1982 | Berner ..................................... | 433/83 |
| 4,391,590 | * 7/1983 | Dougherty .............................. | 433/90 |
| 4,911,639 | * 3/1990 | Jacklich ................................. | 433/102 |
| 5,364,267 | * 11/1994 | Fischer ................................... | 433/26 |
| 5,569,034 | * 10/1996 | Meller et al. ........................ | 433/105 |
| 5,928,154 | * 7/1999 | Silber et al. .......................... | 604/459 |
| 5,967,779 | * 10/1999 | Brassil et al. .......................... | 433/88 |
| 6,164,968 | * 12/2000 | Feine ..................................... | 433/119 |
| 6,193,514 | * 2/2001 | Rahman ................................ | 433/141 |

* cited by examiner

*Primary Examiner*—Ralph A. Lewis
(74) *Attorney, Agent, or Firm*—Daniel N. Lundeen; Lundeen & Arismendi, L.L.P.

(57) ABSTRACT

A color coding system and method for visually identifying and distinguishing ultrasonic dental tool inserts. The invention employs a color-coded removable cap that is used to secure a handgrip, which can also be color-coded, to the insert. The caps and/or handgrips of different inserts thus have different colors to visually distinguish one insert or type of insert from another.

21 Claims, 3 Drawing Sheets

ID SYSTEM FOR ULTRASONIC DENTAL INSERTS

BACKGROUND OF THE INVENTION

This invention relates to ultrasonic dental inserts for dental handpieces, and more particularly to a system for color-coding the inserts to facilitate identification thereof.

Ultrasonic dental tools are commonly used in hygienics, periodontal and other dental procedures. These tools, especially the insert portions thereof that come in contact with the patient, need to be sterilized, usually by autoclaving between procedures. For example, ultrasonic dental tools usually come with a handgrip connected by a cable to water and electrical controls, and a replaceable insert having a magnetostrictive element, a velocity transducer, and a tip. The insert is typically removed from the handpiece for autoclaving between procedures. Depending on the model, the tip and/or magnetostrictive element may be removable from the velocity transducer.

Many different patients may receive treatment from one dental care practitioner in the same day, and there is not usually time to autoclave the tools between procedures, so the practitioner must have several of the same type of tool ready for use. In addition, different ultrasonic dental tools may be used during the same procedure. Often, one set of tools may be used for one type of procedure, whereas a similar set may used for another. Furthermore, in some offices, there may be several practitioners, each having his or her own preference for types of tools for particular procedures.

Frequently, the tools are similar in appearance and difficult to tell apart at a glance, and may require careful inspection. For example, different tools from the same manufacturer may especially have a similar appearance, even though the tools may have subtle differences, e.g. operating frequency. The tools are regularly autoclaved en masse with other tools, or even parts of tools if the tips and/or magnetostrictive elements are removed from the velocity transducers, so quickly identifying ultrasonic dental tools becomes problematic.

The prior art has followed the practice of using colored tape or heat-shrink bands to identify different instruments or parts of instruments. For example, the tools may be marked with the same color adhesive tape or heat shrink band to indicate that they belong to a particular practitioner or operating room, or to indicate that they are for a particular type of procedure. Because the tape and bands serve no mechanical function, it may be difficult to place them on the tools where they will not interfere with the operation of the tools. And since the tape and bands are semi-permanent, it is difficult to remove or alter the color coding, once assigned. Another problem may be that the tape and bands can trap moisture underneath by capillary action, contributing to advanced corrosion or discoloration of the tool and contamination problems.

SUMMARY OF INVENTION

The present invention overcomes the problems noted above by providing a color-coded cap that functions to lock a handgrip into place on the velocity transducer. No additional part or tooling is required, other than coloring the cap, since the cap is already used in the assembly of the ultrasonic dental insert. The cap can be removable by the practitioner so as to allow the color coding of the insert to be readily changed. The ability to remove the cap also serves to prevent the accumulation and/or retention of moisture against metal surfaces to inhibit corrosion and discoloration. For example, the cap can be replaced at very low cost.

The present invention provides a color coding method and system for ultrasonic dental tool inserts by employing a cap that is used to secure an interference-fit handgrip to the insert. The caps of different inserts have different colors to visually distinguish one insert or type of insert from another.

Briefly, the present invention provides a method for identifying ultrasonic dental inserts for use in a dental handpiece. The method comprises the steps of:

(a) selecting an annular cap from a set comprising a plurality of annular caps having differently colored exterior surfaces;

(b) positioning an annular handgrip over an elongated velocity transducer having a proximal end coupled to a magnetostrictive element or provided with a coupling element for removably securing a magnetostrictive element, and a distal end to which an ultrasonic tip is attached or attachable; and (c) engaging the selected cap on an end of the handgrip to form an assembled insert comprising an interference fit between the handgrip and the transducer.

Alternatively, the method can comprise the steps of:

(a) selecting an annular handgrip from a set comprising a plurality of annular handgrips having differently colored exterior surfaces;

(b) positioning the selected annular handgrip over an elongated velocity transducer having a proximal end coupled to a magnetostrictive element or provided with a coupling element for removably securing a magnetostrictive element, and a distal end to which an ultrasonic tip is attached or attachable; and (c) engaging an annular cap on an end of the handgrip to form an assembled insert comprising an interference fit between the handgrip and the transducer.

If necessary, where the proximal end of the velocity transducer includes the coupling element in step (b), the methods can also include the further step of securing a magnetostrictive element to the coupling element. Similarly, where necessary, the methods can also include the further step of securing the tip to the distal end of the velocity transducer. Preferably, the methods further comprise repeating the steps (a), (b) and (c), wherein the caps or handgrips selected in each step (a) comprise at least one respective cap or handgrip differently colored with respect to another cap or handgrip. The differently colored caps and handgrips can be advantageously used to visually distinguish one insert from another. The methods also allow the step of autoclaving the inserts.

In another aspect, the present invention provides a color coding system for ultrasonic dental inserts for use in a dental handpiece. The system includes an insert comprising a magnetostrictive element and a tip operatively coupled to opposite ends of a longitudinal velocity transducer, wherein the magnetostrictive element is adapted to be received in a well in the handpiece. An annular handgrip is disposed about the velocity transducer. An annular cap is provided for concentrically engaging an end of the handgrip and forming an interference fit between the handgrip and the transducer. A colored exterior surface on the cap, the handgrip or a combination thereof, visually distinguishes the insert from a similar insert having a cap, handgrip or combination thereof with a differently colored exterior surface.

In a preferred embodiment of the invention comprising either the system or method, the velocity transducer has opposing ears on either side thereof, the handgrip has opposing recesses formed on inside surfaces of the handgrip for engaging the ears of the velocity transducer, the inside surfaces are movable apart from each other to allow the ears to be inserted into the recesses when the handgrip is positioned over the velocity transducer, and the engagement of the cap prevents the inside surfaces from moving apart to keep the ears in the recesses. The handgrip and the velocity transducer preferably have matching opposing flat surfaces on respective inside and outside surfaces to inhibit rotation of the handgrip with respect to the velocity transducer. The cap preferably has a tapered inside diameter matching an outside diameter of the handgrip. The cap is preferably anodized aluminum.

DETAILED DESCRIPTION

Figure 1:
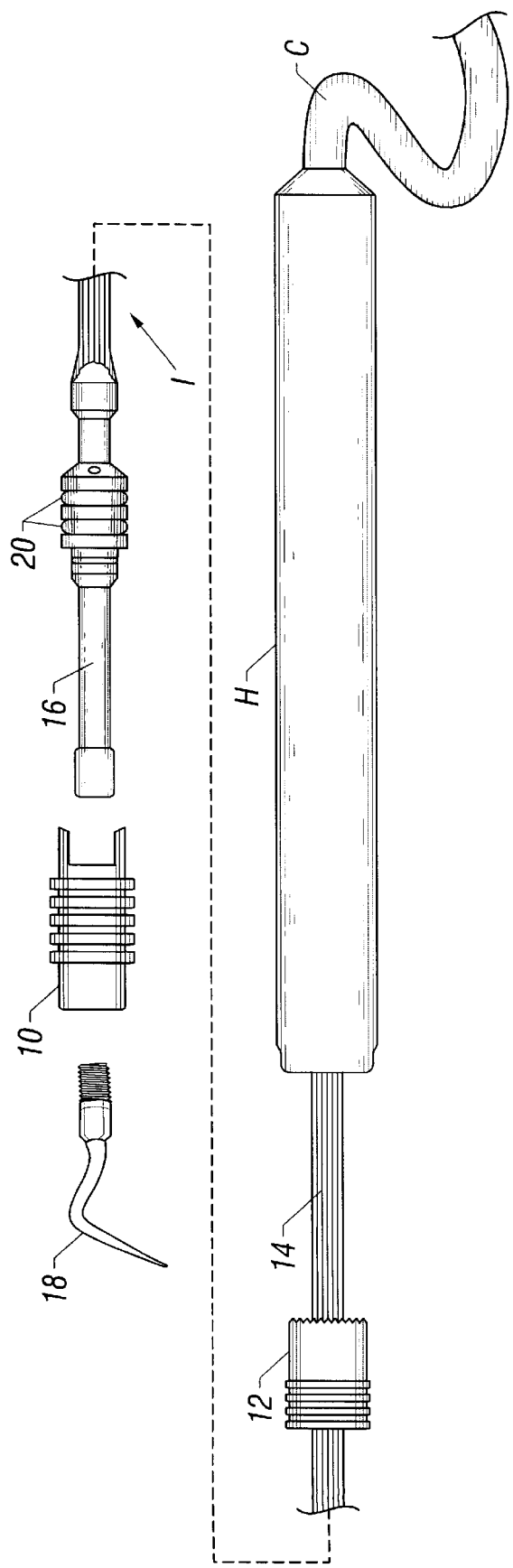
FIG. 1 is an exploded perspective view of an ultrasonic dental insert according to one embodiment of the invention.

With reference to FIGS. 1–5 wherein like numerals are used to reference like parts, the present system and method employ an ultrasonic dental insert /, which is adapted to be received in a handpiece H, in conjunction with an annular handgrip 10 and retaining cap 12. In the present invention, the retaining cap 12 has an exterior surface that is color coded or marked, preferably with a different color than the handgrip 10 and/or the handpiece H so that the one insert/ can be visually distinguished from another.

The handpiece H and insert /can generally be considered conventional in the art. Briefly, the handpiece H has a well for receiving the insert /about which an inductive coil is disposed for imposing an alternating magnetic field that oscillates the magnetostrictive element 14 at an ultrasonic frequency. The ultrasonic vibrations are transmitted from the magnetostrictive element 14 through a velocity transducer 16 and a tip 18, as is well known in the art. Electrical current from a power supply and control unit (not shown) and water are conventionally supplied to a proximal end of the handpiece H via cable C.

Figure 2:
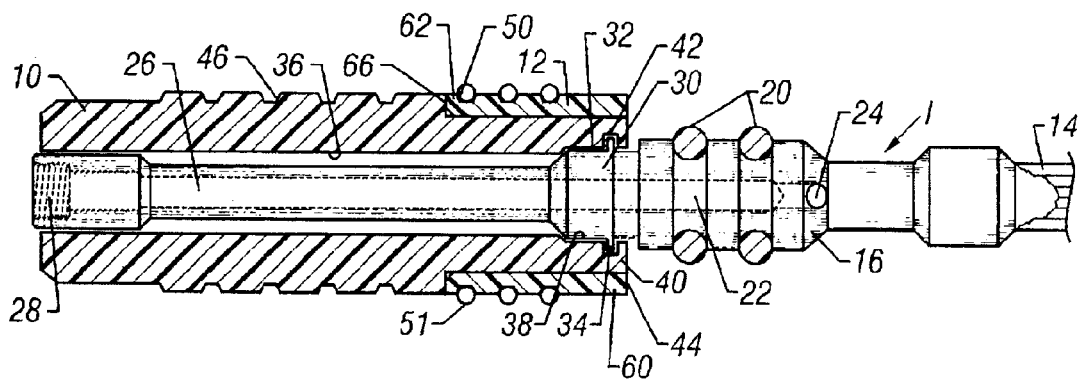
FIG. 2 is a side sectional view, partially cut away, of the assembled ultrasonic dental insert of FIG. 1.
Figure 3:
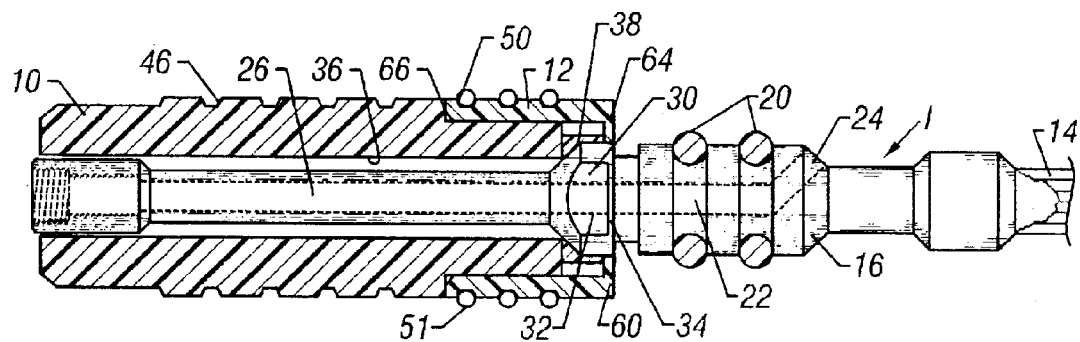
FIG. 3 is another side sectional view, partially cut away, of the ultrasonic dental insert of FIG. 2 rotated 90°.

As best seen in FIGS. 2 and 3, the insert /is typically friction fit into the handpiece H (FIGS. 1 and 5) by means of O-rings 20, which are carried in transverse grooves 22 encircling a medial region of the velocity transducer 16. Thus, the insert /is assembled in the handpiece H by removably sliding the insert / into the handpiece H so that the O-rings 20 engage an inside diameter of the handpiece H. There is usually an opening 24 into a central water supply channel 26(see FIGS. 2–3) positioned on a proximal side of the O-rings 20 so as to allow water to pass from the handpiece H to the tip 18.

The insert /can be of the unitary, two-piece or three-piece design, all of which are known in the art. In the unitary design, the tip 18, velocity transducer 16 and magnetostrictive element 14 are all securely fastened together. In the two- and three-piece designs, the tip 18 is removable, generally by means of threads 28 at a distal end of the velocity transducer 16. In the design of the two-piece insert /, the magnetostrictive element 14 is usually welded or otherwise irremovably attached directly to the proximal end of the velocity transducer 16. In the design of the three-piece insert /, the magnetostrictive element 14 is removably secured to the proximal end of the velocity transducer 16, as described for example, in my earlier U.S. Pat. No. 6,164,968, which is hereby incorporated herein by reference in its entirety as though fully set forth.

The handgrip 10 is provided about the insert /to facilitate holding the instrument by the practitioner. In use, the handgrip 10 must not slide along the insert /or allow rotation of the insert /with respect to the handgrip 10. It is preferred to use a removable handgrip 10 that is secured in place by means of an interference fit and rotational stops. An interference fit is understood in the present specification and claims to mean a mechanism in which a keeper is prevented from leaving a retaining element by limiting their relative movement by suitable emplacement of the cap 12. As is known in the art, the handgrip 10 is made of an autoclavable material such as a thermoplastic or thermoset material, for example polypropylene, acetal resin or the like. Representative handgrip 10 materials are available under the trade designations Delrin, Raydel, Polypenco and the like. The velocity transducer 16 is typically a metal such as stainless steel.

Figure 4:
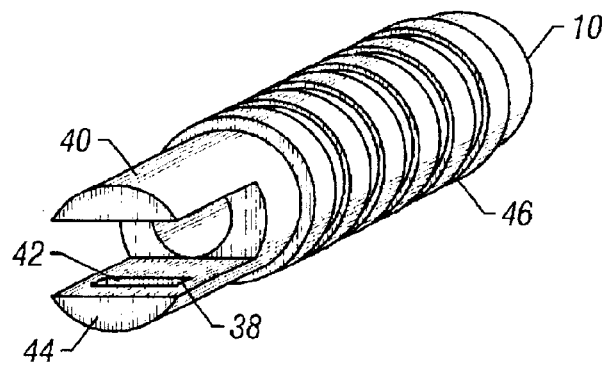
FIG. 4 is an enlarged perspective view of the handgrip seen in FIGS. 1–3.
Figure 5:
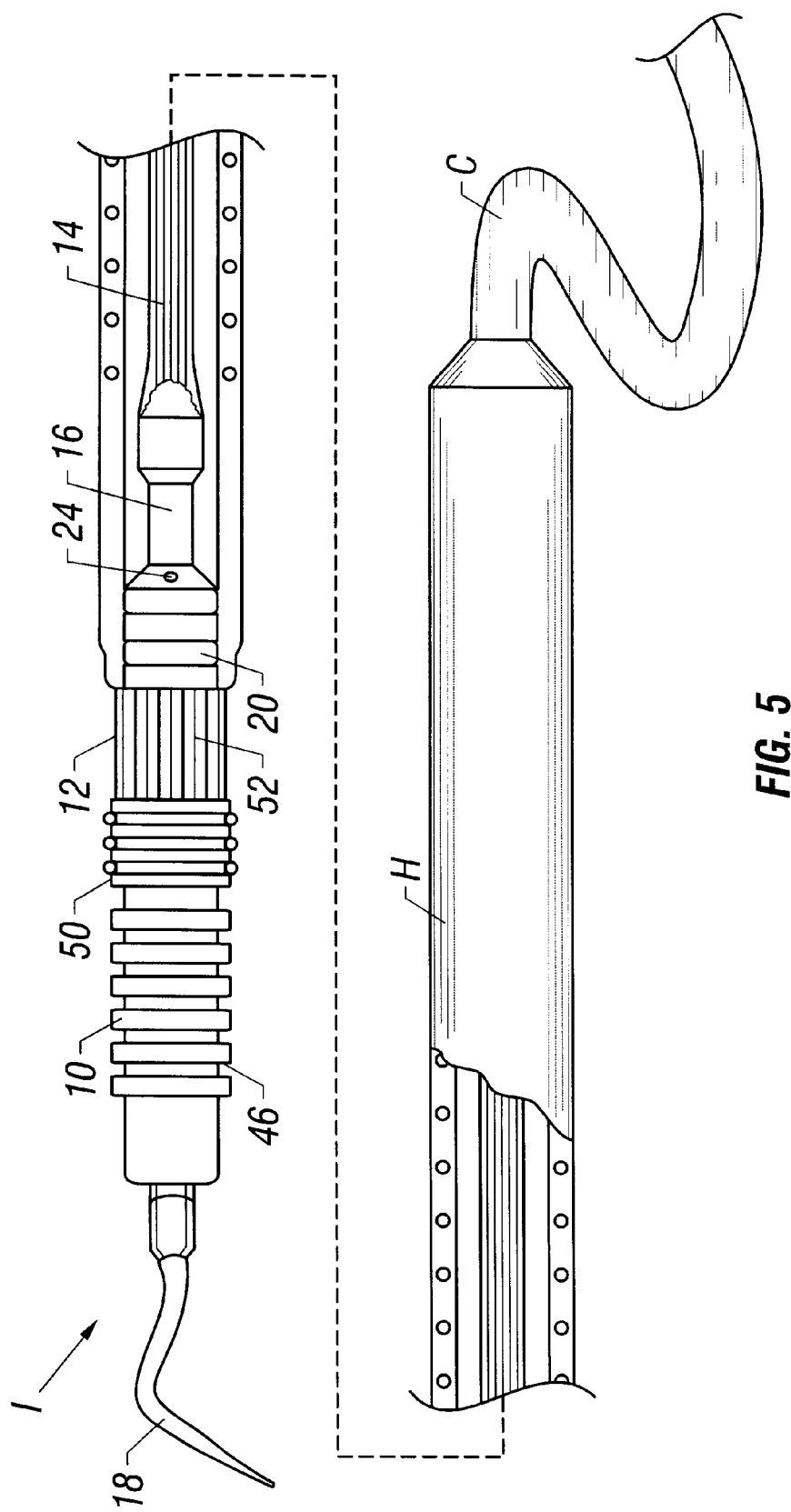
FIG. 5 is a perspective view, partially cut away, of the ultrasonic dental insert of FIGS. 1–4 disposed within a handpiece.

In the preferred embodiment illustrated in FIGS. 3–5, the velocity transducer 16 has a medial section 30 of generally enlarged outside diameter, with partially cut away flats 32 on opposite sides of the medial section 30, leaving a set of ears 34 of uniform outside diameter positioned at a proximal end of each of the flats 32. Forward of the medial section 30, the velocity transducer 16 has a relatively larger outside diameter relative to an inside diameter of a central bore 36 formed through the length of the handgrip 10.

At the proximal end of the handgrip 10, opposing flat surfaces 38 are disposed on opposite arms 40 and dimensioned to match and engage the respective flats 32 of the velocity transducer 16 upon assembly. The interengagement of the respective flats 32 and opposing flat surfaces 38 serves to inhibit rotation of the handgrip 10 with respect to the velocity transducer 16. A radial slot 42 is formed in a proximal end of each flat 32 to have a diameter for receiving a respective ear 34. Preferably, the inside diameter of the radial slot 42 is slightly larger than the outside diameter of the ears 34 when the arms 40 are not biased or under compression by the cap 12. A respective lip 44 on the proximal end of each arm 40 serves to keep each respective ear 34 in interengagement with the respective radial slot 42 to inhibit longitudinal movement of the handgrip 10 with respect to the velocity transducer 16. The arms 40 and the proximal end of the handgrip 10 are preferably formed with a uniform outside diameter. The outside surface of the handgrip 10 can include knurls or grooves 46 formed thereon to facilitate grasping of the handgrip 10 by the dental practitioner.

The cap 12 is preferably aluminum, which can be anodized to have a color selected from a wide range of different colors, but could also be stainless steel, thermoplastic polymer, thermoset polymer, or the like. The cap 12 has a generally circular cylindrical exterior surface of uniform diameter and can also have radial grooves 50 and/or longitudinal knurls 52 to facilitate grasping by the dental practitioner. The grooves 50 can receive rubber or plastic rings 51 of various colors for identification purposes. The cap 12 also includes a central longitudinal bore formed through proximal end 60 thereof that has an inside diameter matching the outside diameter of the medial section 30 of the velocity transducer 16 so that the cap 12 can slide freely over the proximal end of the velocity transducer 16 after the handgrip 10 has been positioned with the ears 34 in the respective slots 42. The cap 12 has a distal end 62 with an inside diameter matching the outside diameter of the proximal end 60 of the handgrip 10, preferably a slightly smaller diameter than that of the handgrip 10, and especially a diameter tapered from a diameter about the same as that of the handgrip 10 adjacent the distal end 62 (e.g. 0.345 inches) to a diameter slightly smaller than that of the handgrip 10 adjacent the proximal end 60 (e.g. 0.340 inches). At the proximal end 60 of the cap 12, there are opposing lips 64 that extend inwardly to complement the gap between the arms 40 and inhibit rotation of the cap 12 with respect to the handgrip 10. The spacing of the opposing lips 64 is preferably less than an outside diameter of the distal end of the handpiece H so that the placement of the insert /within the handpiece H further facilitates holding the cap 12 in place over the handgrip 10. The distal end 62 can also have an outwardly tapered chamfer 66 to facilitate guiding and sliding the cap 12 into place over the proximal end of the handgrip 10. As an alternative design not illustrated, the cap 12 can be threadedly engaged over an exterior surface of the handgrip 10.

To assemble the insert /, if necessary, the tip 18 and the magnetostrictive element 14 can be attached to the respective distal and proximal ends of the velocity transducer 16, either before or after the handgrip 10 and cap 12 are positioned on the velocity transducer 16; however, if either presents a larger outside diameter than the inside diameter of the handgrip 10, they can be attached after the handgrip 10 and/or cap 12 are so positioned. Typically, the handgrip 10 is positioned on the velocity transducer 16 before the tip 18 since it will not usually slide over the tip 18, but the cap 12 can usually be slid over the magnetostrictive element 14 without difficulty. To attach the handgrip 10 of the selected exterior color to the velocity transducer 16, the proximal end of the selected handgrip 10 is slipped over the distal end of the velocity transducer 16, the handgrip 10 is rotated to align the flats 32 with the flat surfaces 38, and the arms 40 are positioned to engage the ears 34 in the slots 42. The cap 12 of suitable exterior color configuration is selected and then friction fit into place over the proximal end of the handgrip 10 to prevent the ears 34 from disengaging from the retaining slots 42. The O-rings 20 can be positioned in the grooves 22 on the velocity transducer 16 either before or after the cap 12. When the insert /is positioned in the handpiece H, the cap 12 is further secured in place by the lip 64 disposed between the distal end of the handpiece H and the proximal end of the handgrip 10.

By selecting the exterior color configuration of the handgrip 10 or cap 12, or color configuration combination of the handgrip 10 with the cap 12, the ultrasonic dental inserts /can be readily distinguished from a number of similar dental inserts by visual means. The color configuration can be used to identify features or characteristics of the insert /selected from the type of insert /(e.g. the type of tip 18), the dental practitioner who uses or owns the insert /, the frequency of the operation of the insert /, or the like. For example, inserts /operable at a first frequency can use caps 12 with green rings 51; inserts /operable at a second frequency, red rings 51; and inserts /operable at a third frequency, purple rings 51. At the same time, for example, the handgrips 10 used with inserts /of one type of tip 18 can be green; with a second type, orange; and a third type, brown or black. Inserts /used by a first dental practitioner can be identified with a combination of pink and yellow rings 51, by a second with a combination of green and blue rings 51, and by a third by a combination of red and orange rings 51. Other variations on these color-coding examples will be apparent to the skilled artisan.

The above description is only illustrative of embodiments of the invention. Various changes and modifications of these embodiments will occur to the skilled artisan in view of the preceding specification. It is intended that all such modifications and changes within the scope and spirit of the appended claims be embraced thereby.

What is claimed is:

1. A method for identifying ultrasonic dental inserts for use in a dental handpiece having an induction coil disposed about a well, comprising the steps of:
   (a) selecting an annular cap from a set comprising a plurality of annular caps having differently colored exterior surfaces;
   (b) positioning an annular handgrip over an elongated velocity transducer having a proximal end, coupled to a magnetostrictive element or provided with a coupling element for removably securing a magnetostrictive element, and a distal end to which an ultrasonic tip is attached or attachable;
   (c) engaging the selected cap on an end of the handgrip to form an assembled insert comprising an interference fit between the handgrip and the transducer.

2. The method of claim 1, wherein the proximal end of the velocity transducer includes the coupling element in step (b), and the method comprises the further step of securing a magnetostrictive element to the coupling element.

3. The method of claim 1, wherein the method comprises the further step of securing the tip to the distal end of the velocity transducer.

4. The method of claim 1, further comprising repeating said steps (a), (b) and (c) wherein the caps selected in each step (a) comprise at least one cap differently colored with respect to another cap.

5. The method of claim 4, wherein the differently colored caps are used to visually distinguish one insert from another.

6. The method of claim 5 wherein the caps have colored identifying rings supported in radial grooves of an exterior surface.

7. The method of claim 5, further comprising the step of autoclaving the inserts.

8. The invention of claim 1, wherein the velocity transducer has opposing ears on either side thereof, the handgrip has opposing recesses formed on inside surfaces of the handgrip for engaging the ears of the velocity transducer, the inside surfaces are moveable apart from each other, and the engagement of the cap prevents the inside surfaces from moving apart to keep the ears in the recesses.

9. The invention of claim 8 wherein the cap has a tapered inside diameter matching an outside diameter of the handgrip.

10. A method for identifying ultrasonic dental inserts for use in a dental handpiece having an induction coil disposed about a well, comprising the steps of:
   (a) selecting an annular handgrip from a set comprising a plurality of annular handgrips having differently colored exterior surfaces;
   (b) positioning the selected handgrip over an elongated velocity transducer having a proximal end, coupled to a magnetostrictive element or provided with a coupling element for removably securing a magnetostrictive element, and a distal end to which an ultrasonic tip is attached or attachable;

(c) engaging an annular cap on an end of the handgrip to form an assembled insert comprising an interference fit between the handgrip and the transducer.

11. The method of claim 10, wherein the proximal end of the velocity transducer includes the coupling element in step (a), and the method comprises the further step of securing a magnetostrictive element to the coupling element.

12. The method of claim 10, wherein the method comprises the further step of securing the tip to the distal end of the velocity transducer.

13. The method of claim 10, further comprising repeating said steps (a), (b) and (c) wherein the handgrips selected in each step (a) comprise at least one handgrip differently colored with respect to another handgrip.

14. The method of claim 13, wherein the differently colored handgrips are used to visually distinguish one insert from another.

15. The method of claim 14 wherein the handgrips have colored identifying rings supported in radial grooves of an exterior surface thereof.

16. The method of claim 15, further comprising the step of autoclaving the inserts.

17. A system for identifying ultrasonic dental inserts for use in a dental handpiece having an induction coil disposed about a well, comprising:

means for positioning an annular handgrip over an elongated velocity transducer having a proximal end, coupled to a magnetostrictive element or provided with a coupling element for removably securing a magnetostrictive element, and a distal end to which an ultrasonic tip is attached or attachable;

means for removably engaging a selected annular cap on an end of the handgrip to form an assembled insert comprising an interference fit between the handgrip and the transducer, wherein the cap is selected from a set comprising a plurality of annular caps having differently colored exterior surfaces.

18. A color coding system for ultrasonic dental inserts for use in a dental handpiece having an induction coil disposed about a well, comprising:

an insert comprising a magnetostrictive element and a removable tip operatively coupled to opposite ends of a longitudinal velocity transducer, wherein the magnetostrictive element is adapted to be received in the well;

an annular handgrip removably disposed about the velocity transducer;

a removable annular cap for concentrically engaging an end of the handgrip and forming an interference fit between the handgrip and the transducer;

a colored exterior surface on the handgrip or cap for visually distinguishing the insert from a similar insert having a handgrip or cap with a differently colored exterior surface.

19. The invention of claim 18, wherein the velocity transducer has opposing ears on either side thereof, the handgrip has opposing recesses formed on inside surfaces of the handgrip for engaging the ears of the velocity transducer, the inside surfaces are moveable apart from each other, and the engagement of the cap prevents the inside surfaces from moving apart to keep the ears in the recesses.

20. The invention of claim 18 wherein the cap has a tapered inside diameter matching an outside diameter of the handgrip.

21. The invention of claim 18 wherein the caps have colored identifying rings supported in radial grooves of an exterior surface.

* * * * *